United States Patent [19]

Quint

[11] 4,163,300

[45] Aug. 7, 1979

[54] ELECTRIC TOOTHBRUSH

[76] Inventor: Hugh D. Quint, Rte. #2, Box 90 C, Osceola, Mo. 64776

[21] Appl. No.: 882,368

[22] Filed: Mar. 1, 1978

[51] Int. Cl.² ............................................. A46B 13/02
[52] U.S. Cl. ...................................... 15/23; 200/1 V; 200/61.52; 200/153 A
[58] Field of Search ..................... 15/23, 24; 200/1 V, 200/61.52, 153 A, 157

[56] References Cited

U.S. PATENT DOCUMENTS

| 2,279,982 | 4/1942 | Glynn | 15/23 |
| 2,310,626 | 2/1943 | Gold | 15/23 |
| 2,618,797 | 11/1952 | Grover | 15/23 |
| 3,161,899 | 12/1964 | Poizat | 15/23 |

Primary Examiner—Edward L. Roberts
Attorney, Agent, or Firm—John A. Hamilton

[57] ABSTRACT

An electric toothbrush consisting of an elongated body member having a cylindrical brush mounted coaxially therewith at one end thereof, and driven rotatably by a reversible electric motor carried in the handle, and having an automatic reversing switch responsive to the position in which the handle is held to cause rotation of the brush such that its bristles move in a direction from the gum line toward the crowns of the teeth.

5 Claims, 5 Drawing Figures

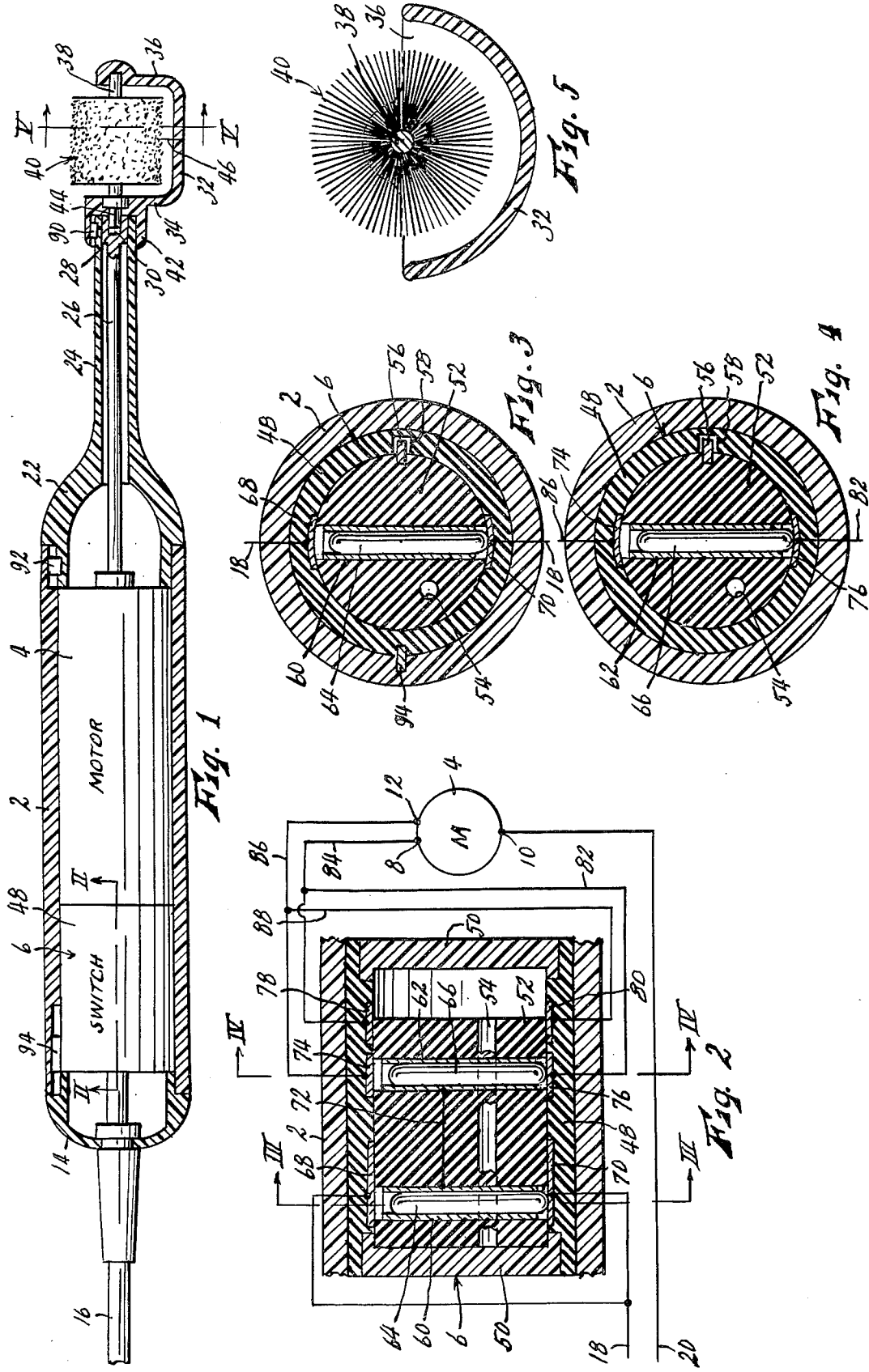

ELECTRIC TOOTHBRUSH

This invention relates to new and useful improvements in toothbrushes, and has as its principal object the provision of an electric toothbrush so arranged and controlled that when brushing the side surfaces of the teeth, the bristles of the brush always move in a direction from the gum line toward the crowns of the teeth, the reversals of movement of the brush which are necessary when transferring it between the inner and outer sides of the teeth, or between the upper and lower teeth, being accomplished by a reversing switch automatically responsive to the various positions in which the brush handle is naturally held to gain access to various portions of the mouth.

It has long been known that from the viewpoint of good dental hygiene, it is desirable to so manipulate a toothbrush that its bristles move away from the gum line toward the crowns of the teeth, that is, downwardly on the upper teeth and upwardly on the lower teeth. Bristle movement in the opposite direction has the tendency in many instances to force food particles and other dental debris under the gums, that is, between the gums and the tooth surfaces, where such particles may become trapped more or less permanently and hence become a cause of future tooth decay. Instructions in the proper use of ordinary manual toothbrushes usually include directions to use a brush in this manner, i.e. so that its bristles engage the teeth only when moving away from the gum line. However, the manual manipulation of the brush thus required is quite awkward and difficult at best, with the result that such directions are often ignored, or observed only occasionally and casually. On the other hand, the brush movement in virtually all electric toothbrushes within my knowledge is oscillatory or reciprocatary, with the result that half of the brush strokes are in the "wrong" direction, that is, in a direction tending to cause lodgment of food particles under the gums. The present electric toothbrush overcomes all of these defects of manual toothbrushes, and prior electric toothbrushes, in a simple, effective manner.

More specifically, the objects of the present invention include first, the provision of an electric toothbrush including a cylindrical brush coaxial with its line of insertion into the mouth, and usually rotatable about its axis in one direction whereby its bristles move from the gum line toward the teeth crowns when applied to certain tooth surfaces, second the provision of means for reversing the direction of brush rotation when desired so that the desired brushing direction may be maintained on all tooth surfaces, and third the provision of means whereby the brush reversals are accomplished automatically without requiring conscious operations by the user. A special guard partially surrounding the brush serves the dual functions both of protecting the inner surfaces of the cheeks and lips against the abrasive action of the brush, and also of requiring the user to make certain adjustments in the position of the brush which are necessary to the operation of the brush reversal means.

With these objects in view, as well as other objects which will appear in the course of the specification, reference will be had to the accompanying drawing, wherein:

FIG. 1 is a partially schematic longitudinal sectional view through an electric toothbrush embodying the present invention, with parts left in elevation, FIG. 2 is a partially schematic sectional view taken on line II—II of FIG. 1, showing the reversal control switch, and including a schematic wiring diagram of the electric motor, FIG. 3 is a sectional view taken on line III—III of FIG. 2, FIG. 4 is a sectional view taken on line IV—IV of FIG. 2, and FIG. 5 is an enlarged sectional view taken on line V—V of FIG. 1.

Like reference numerals apply to similar parts throughout the several views. The electric toothbrush forming the subject matter of the present invention includes a tubular cylindrical body member 2, formed of plastic, or any other suitable material, and containing an electric motor 4 coaxially in the forward portion thereof, and a reversing control switch indicated generally by the numeral 6 in the rearward portion thereof. The switch will be described in detail hereinbelow. The motor is of a reversible type, the specific details of which are not pertinent to the present invention, which will turn in one direction when electric current is supplied thereto across terminals 8 and 10 (see FIG. 2), and in the opposite direction when current is supplied across terminals 12 and 10.

The rearward end of the body member is closed by a cap 14 through which projects a trailing flexible cable 16 carrying the electric line wires 18 and 20 for supplying current to the motor. The forward end of the body member is closed by a cap 22 which extends forwardly to form a tubular neck 24 of reduced diameter. The drive shaft 26 of motor 4 projects coaxially through neck 24, and is provided at its forward end with an enlarged head 28 rotatable in the neck and flush with the forward end thereof. A squared socket 30 is formed coaxially in the forward end of head 28.

A generally semi-cylindrical brush guard 32, coaxial with the neck and also formed of plastic or the like, is carried at the forward end of neck 24. Said guard has rearward and forward end walls 34 and 36. A brush spindle 38 is disposed coaxially within the guard, being journalled rotatably in said end walls, and carries bristles suitably affixed thereto and extending radially therefrom, whereby to form a generally cylindrical brush 40 of which about one-half is disposed within the guard, and one-half projects outwardly from the guard at one side. Inner end wall 34 of the guard is formed to present a rearwardly opening socket portion 42 which is engaged slidably and frictionally over the forward end of neck 24, and a squared end portion 44 of brush spindle 38 projects rearwardly into said socket for axial sliding engagement in socket 30 of motor shaft 26. Thus the entire brush head, consisting of guard 32, brush 40 and its spindle 38 may be easily detached from the neck, so that the device may be used by different persons simply by interchanging brush heads. The guard may be formed originally in two halves, divided transversely along line 46 indicated in FIG. 1, with the halves being united and permanently joined after the brush and its spindle have been assembled therein.

Reversing switch 6, as shown in exemplary fashion in FIGS. 2-4, includes a cylindrical housing 48, formed of electrical insulating material, inserted snugly in the rearward portion of body member 2, being motor 4. The ends of housing 48 are closed by end walls 50.

Disposed in said housing for free axial sliding movement therein is a solid cylindrical core 52, also formed of insulating material. Its sliding movement in the housing is limited by end walls 50, and it has a hole 54 formed therethrough parallel to its axis so that air pressure therein cannot interfere with its free sliding movement. It is prevented from turning on its axis within the housing by a key 56 (see FIGS. 3 and 4) fixed therein and engaged loosely in a groove 58 formed longitudinally in the inner surface of the housing.

Extending diametrically through core 52, at respectively rearward and forward points thereof, are a pair of tubular sleeves 60 and 62 formed of electrical conducting material, and disposed respectively therein are a pair of plugs 64 and 66 also formed of conducting material. Said plugs are freely slidable in said sleeves, but are of insufficient length to extend completely through core 52. Set into the inner surface of housing 48, in alignment with the opposite ends of sleeve 60, are a pair of electrical contacts 68 and 70, adapted to be engaged by one or the other of the ends of plug 64, that end thereof which happens to be lowermost in the position in which body member 2, which also serves as a handle, is held at any given moment. Contacts 68 and 70 are of sufficient length longitudinally of the core, that plug 64 can engage them whether the core is in its rearmost position, as shown in FIG. 2, or in its forwardmost position. It moves to its rearward position whenever the device is held so that its main axis slopes upwardly toward brush 40, and moves to its forward position whenever said major axis slopes downwardly toward the brush. Lead wire 18 is connected to both of contacts 68 and 70, and sleeve 62 is connected to sleeve 60 by wire 72. Therefore, sleeve 62 is electrically connected to lead wire 18 regardless of the position in which the assembly is held. Lead wire 20 is directly connected to motor terminal 10. The purpose of the sliding gravity-actuated contact provided by plug 64 is to obviate any interference thereby with the sliding movement of core 52.

When core 52 is in its rearward position, as shown in FIG. 2, plug 66 engages either a contact 74 or a contact 76, said contacts 74 and 76 being fixed in the interior surface of housing 48 in diametric alignment with each other, depending on which end of the plug is lowermost in any position the device is held at a given moment. When core 52 is in its forward position, plug 66 cooperates in like manner with a pair of diametrically opposed contacts 78 and 80 mounted in housing 48 similarly to contacts 74 and 76. Contacts 76 and 78 are connected by wires 82 and 84 to motor terminal 8. Contacts 74 and 80 are connected by wires 86 and 88 to motor terminal 12. Since as will appear it is essential that the transverse plane of the device established by plugs 64 and 66 be coincident with or parallel to the plane of the open side of brush guard 32, keys 90, 92 and 94 are provided respectively at the connection of brush guard socket 42 to neck 24, at the connection of forward body cap 22 into body member 2, and interconnecting switch housing 48 into body member 2, thus insuring in each case that the related elements can be assembled in only one angular relation. In this manner, the keys 90, 92 and 94, together with key 56 guiding switch core 52 in housing 48, insure the proper relationship of plugs 64 and 66 to brush guard 32. It will be understood also that body member 2 could also be provided if desired with a simple manually controlled on-off switch disposed in the motor circuit, although this is not pertinent to the present invention. This on-off control could also be provided by a switch mounted in cable 16, or simply plugging or unplugging said cable from an electric wall outlet.

In describing the operation of the device, the directions of brush rotation, and relatively left-facing and right-facing tooth surfaces, will be described as viewed from the vantage point of body member 2, looking forwardly toward brush 40. It will of course be understood that line wire 20 is always connected to common motor terminal 10, and that line wire 18 is always connected to switch plug 66 through one or the other of contacts 68 and 70, plug 64, sleeve 60, wire 72 and sleeve 62, regardless of the position in which the brush may be held.

If the brush is held naturally by the user and inserted into the mouth to clean the upper teeth, it will normally be held with its axis inclined upwardly into the mouth, and with the rearward end of body member 2 in a relatively lower position. This causes switch core 52 to slide to its rearward position by gravity, bringing switch plug 66 into cooperating relationship with contacts 74 and 76. If the brush is applied to a right-facing side surface of an upper tooth, the body member must be turned on its axis to position guard 32 in a left-opening position, in order that the brush can engage the tooth surface. This positioning of the body member causes switch plug 66 to slide downwardly in sleeve 62 to engage contact 76, so that electric current is supplied to the motor across terminals 8 and 10 thereof. This causes rotation of brush 40 in a counter-clockwise direction, so that the brushing direction of the brush bristles is downward, or in a gum-to-crown direction, as desired. If, on the other hand, the brush is applied to a left-facing side surface of the upper teeth, this requires angular inversion of the body member about its axis, to bring the exposed side of brush 40 into engagement with the teeth. This inversion causes plug 66 to slide downwardly in sleeve 62 to engage contact 74, so that current is supplied to the motor across terminals 12 and 10. The direction of brush rotation is thus reversed to clockwise, so that the brush movement over the teeth is still downward, or in the desired gum-to-crown direction.

On the other hand, if the body member 2, which of course is also the handle by which the device is manipulated, is held naturally by the user and brush 40 inserted into the mouth to clean the lower teeth, it will normally be held with its axis inclined downwardly into the mouth, with the rearward end of the body member disposed at a higher elevation than brush 40. This causes switch core 52 to slide to its forward position by gravity, so that plug 66 cooperates with contacts 78 and 80, rather than contacts 74 and 76 as before. The polarity of contacts 78 and 80 relative to motor terminals 8 and 12, is reversed as compared to their respectively corresponding contacts 74 and 76, contact 78 being connected to terminal 8 rather than terminal 12 as is contact 74, and contact 80 being connected to terminal 12 rather than to terminal 8 as is contact 76. Thus when guard 32 is opened to the left to engage right-facing tooth surfaces, contact 80 comes into use to produce clockwise rotation of the brush, and when the handle is angularly inverted to open guard 32 to the right to apply the brush to left-facing tooth surfaces, contact 78 comes into play to cause counter-clockwise rotation of the brush. Thus, when brushing any side surfaces of the lower teeth, the direction of brush action against the teeth is always in an upward direction, or from the gums toward the tooth crowns as desired. Thus, the necessary reversals of rotation of the brush, in order to provide the desired gum-to-crown direction of brush action against the teeth, are accomplished fully automatically by the gravity-responsive action of switch 6, with no conscious actions or manipulations by the user. When brushing the crowns or "bite surfaces" of the molars, it makes little difference which way brush 40 turns. Switch plugs 64 and 66 may then be generally horizontal, but it is extremely unlikely that they will be precisely horizontal, and therefore so long as switch core 52 is freely slidable in housing 48, and so long as the plugs are freely slidable in their sleeves 60 and 62, each plug will virtually always be in electrical engagement with one or the other of the fixed contacts cooperating therewith.

Brush guard 32 of course is always positioned to guard the inner surfaces of the user's lips and cheeks against the possibly painful scrubbing action of the brush bristles. However, from the direct viewpoint of the primary function of the guard is that it necessitates the angular inversion of body member 2 when shifting the brush between left-facing and right-facing tooth surfaces, in order to provide the required reversals of brush rotation.

While I have shown and described a specific embodiment of my invention, it will be readily apparent that many minor changes of structure and operation could be made without departing from the spirit of the invention.

What I claim as new and desire to protect by Letters Patent is:

1. An electric toothbrush comprising:
   a. an elongated body member adapted to serve as a handle whereby the device is manually held and manipulated,
   b. a generally cylindrical brush carried by said body member at one end thereof, said brush being disposed generally coaxially with said body member and being mounted thereon for rotation about its axis,
   c. a reversible electric motor mounted in said body member and operable to rotate said brush selectively in opposite directions, and
   d. reversing switch means carried by said body member and operable to reverse the direction of rotation of said motor, said reversing switch means being operable responsively to gravity-induced movement of an element thereof to cause respectively opposite directions of said motor depending on whether said body member is held in a position with its axis inclined upwardly toward said brush, or downwardly toward said brush.

2. An electric toothbrush as recited in claim 1 wherein said reversing switch means also operates responsively to gravity-induced movement of elements thereof to cause reversals of the direction of rotation of said motor whenever said body member is turned angularly about its axis between first and second positions angularly spaced apart by about 180 degrees.

3. An electric toothbrush as recited in claim 2 with the addition of a brush guard of hollow, generally semi-cylindrical form carried fixedly by said body member to partially enclose said brush in generally coaxial relation thereto, the plane of the open side of said brush guard being generally parallel to a longitudinal transverse plane of said body member established by said first and second angular positions thereof.

4. An electric toothbrush as recited in claim 2, the direction of rotation of said brush, when looking from said body member toward said brush, being clockwise when said brush guard opens laterally to the right and said body axis is inclined upwardly toward the brush, or when the guard opens to the left and the body axis is inclined downwardly toward the brush, and being counter-clockwise when the brush guard opens laterally to the left and the body axis is inclined upwardly toward the brush, or when the guard opens to the right and the body axis is inclined downwardly toward the brush.

5. An electric toothbrush as recited in claim 2 wherein said reversing switch means comprises:
   a. a hollow cylindrical switch housing of insulating material mounted coaxially in said body member,
   b. a cylindrical switch core of insulating material disposed for axial sliding movement, but not rotary movement, in said housing, so as to slide toward said brush to a first position when the body axis is inclined downwardly toward said brush, and away from said brush to a second position when the body axis is inclined upwardly toward the brush,
   c. a conducting switch plug carried for diametrical sliding movement in said switch core, and connected at all times to an electric line wire supplying said motor,
   d. first and second contacts mounted interiorly in said switch housing in diametrically opposed relation and operable to be engaged selectively by said plug, depending on which of said contacts is lowermost in the position in which the body member is held, whenever said switch core is in said first position,
   e. third and fourth contacts mounted interiorly in said switch housing in angularly corresponding, but longitudinally offset, relation respectively to said first and second contacts, so as to be engaged selectively by said plug when said switch core is in said second position, engagement of said plug with either of said first and fourth contacts completing a motor circuit causing rotation thereof in one direction, and engagement of said plug with either of said second and third contacts completing a motor circuit causing rotation thereof in an opposite direction.

* * * * *